United States Patent [19]

Fernandes et al.

[11] Patent Number: 4,604,377

[45] Date of Patent: * Aug. 5, 1986

[54] PHARMACEUTICAL COMPOSITIONS OF MICROBIALLY PRODUCED INTERLEUKIN-2

[75] Inventors: Pete M. Fernandes, Lafayette; Terrance A. Taforo, Oakland, both of Calif.

[73] Assignee: Cetus Corporation, Emeryville, Calif.

[*] Notice: The portion of the term of this patent subsequent to Jul. 23, 2002 has been disclaimed.

[21] Appl. No.: 715,152

[22] Filed: Mar. 21, 1985

Related U.S. Application Data

[63] Continuation-in-part of Ser. No. 594,350, Mar. 28, 1984, abandoned.

[51] Int. Cl.$^4$ ............ A61K 45/02; A61K 37/02; A61K 39/39; C07K 13/00
[52] U.S. Cl. .................................. 514/8; 530/351; 424/85; 424/87; 424/88; 435/68; 435/70; 435/172.3; 435/240; 435/241; 435/948; 514/2; 935/11; 935/12
[58] Field of Search ............ 260/112 R; 435/68, 70, 435/172.3, 948; 424/85, 88, 87; 935/11, 12; 514/2, 8

[56] References Cited

U.S. PATENT DOCUMENTS

| | | | |
|---|---|---|---|
| 4,401,756 | 8/1983 | Gillis | 435/68 |
| 4,490,289 | 12/1984 | Stern | 260/112 R |
| 4,518,584 | 5/1985 | Mark et al. | 260/112 R X |
| 4,530,787 | 7/1985 | Shaked et al. | 260/112 R |

OTHER PUBLICATIONS

Morgan et al., Science (1976), 193:1007–1008.
Taniguchi et al., Nature (1983), 302, 305–310.
Devos et al., Nucleic Acids Research (1983), 11, 4307–4323.

Primary Examiner—Howard E. Schain
Attorney, Agent, or Firm—Albert P. Halluin

[57] ABSTRACT

A sterile, stable lyophilized formulation of selectively oxidized microbially produced recombinant IL-2 in which the recombinant IL-2 is admixed with a water soluble carrier such as mannitol that provides bulk, and a sufficient amount of sodium dodecyl sulfate to ensure the solubility of the recombinant IL-2 in water. The formulation is suitable for reconstitution in aqueous injections for parenteral administration and it is stable and well tolerated in human patients. FIG. 1 illustrates a preferred method of purifying recombinant IL-2 suitable for use in preparing the formulations of the present invention.

15 Claims, 1 Drawing Figure

PHARMACEUTICAL COMPOSITIONS OF MICROBIALLY PRODUCED INTERLEUKIN-2

CROSS REFERENCE TO RELATED APPLICATIONS

This application is a continuation-in-part of U.S. Ser. No. 594,350, filed Mar. 28, 1984, now abandoned, the disclosure of which is incorporated herein by reference. This application is related to U.S. application Ser. Nos. 564,224, now U.S. Pat. No. 4,518,584 filed Dec. 20, 1983; 594,351, filed Mar. 28, 1984, now abandoned, 661,902filed Oct. 17, 1984, now U.S. Pat. No. 4,530,787; 594,223, filed Mar. 28, 1984; 594,250, filed Mar. 28, 1984; the disclosures of which are incorporated herein by reference.

TECHNICAL FIELD

This invention is in the field of pharmaceuticals. More particularly, it relates to pharmaceutical formulations of microbially produced interleukin-2.

BACKGROUND ART

Interleukin-2, a lymphokine which is produced by normal peripheral blood lymphocytes and induces proliferation of antigen or mitogen stimulated T cells after exposure to plant lectins, antigens, or other stimuli, was first described by Morgan, D. A., et. al., Science (1976) 193:1007-1008. Then called T cell growth factor because of its ability to induce proliferation of stimulated T lymphocytes, it is now recognized that in addition to its growth factor properties it modulates a variety of functions of immune system cells in vitro and in vivo and has been renamed interleukin-2 (IL- 2). IL-2 is one of several lymphocyte-produced messenger-regulatory molecules that mediate immunocyte interactions and functions.

IL-2 was initially made by cultivating human peripheral blood lymphocytes (PBL) or other IL-2-producing cell lines. See, for instance, U.S. Pat. No. 4,401,756. Recombinant DNA technology has provided an alternative to PBLs and cell lines for producing IL-2. Taniguchi, T., et al., Nature (1983) 302:305-310 and Devos, R., Nucleic Acids Research (1983) 11:4307-4323 have reported cloning the human IL-2 gene and expressing it in microorganisms.

Belgian Pat. No. 898,016, granted Nov. 14, 1983 and U.S. application Ser. No. 564,224 (U.S. Pat. No. 4,518,584 granted May 21, 1985) describe muteins of IL-2 in which the cysteine normally occurring at position 125 of the wild-type or native molecule has been deleted or replaced with a neutral amino acid, such as serine. These muteins possess IL-2 biological activity. The Belgian patent states that the recombinant muteins may be formulated and administered as with native IL-2 by combining them with aqueous vehicles and injecting them intravenously, subcutaneously, or the like.

DISCLOSURE OF THE INVENTION

One aspect of the present invention is an IL-2 composition suitable for reconstituting in a pharmaceutically acceptable aqueous vehicle for parenteral administration to a patient to provide IL-2 therapy comprising a sterile lyophilized mixture of:

(a) a therapeutically effective amount of oxidized microbially produced recombinant IL-2 that is substantially free of non-IL-2 protein;

(b) a pharmaceutically acceptable water soluble carrier that does not affect the stability of the microbially produced IL-2 adversely; and (c) a sufficient amount of surface active agent such as alkali metal sulfates, e.g., sodium dodecyl sulfate (SDS), alkali metal sarcosinates or sodium deoxycholate to ensure the water solubility of the microbially produced recombinant IL-2.

Preferably, the recombinant IL-2 has been selectively oxidized such that the cysteines at positions 58 and 105 form a disulfide bond to render the molecule biologically active.

Another aspect of this invention is a pharmaceutical composition for providing therapy to a patient comprising a sterile solution of:

(a) the above described mixture dissolved in (b) a pharmaceutically acceptable aqueous parenteral vehicle, said solution containing in the range of about 0.01 mg to about 2 mg of the microbially produced recombinant IL-2 per ml.

MODES FOR CARRYING OUT THE INVENTION

Figure 1:
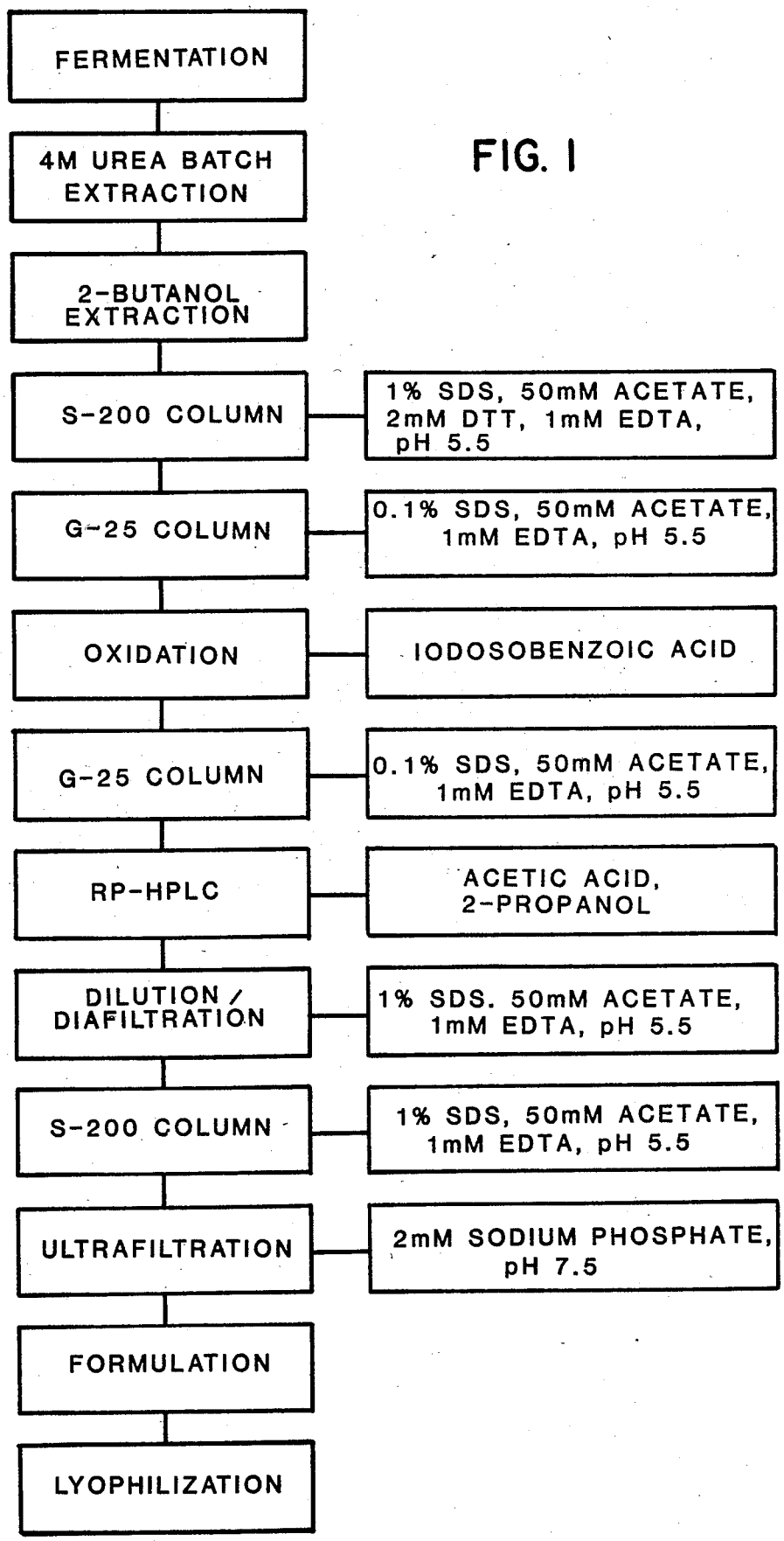
FIG. 1 is a flow diagram of a preferred procedure for processing and purifying microbially produced recombinant IL-2.

As used herein the term "IL-2" denotes an unglycosylated protein that is produced by a microorganism that has been transformed with a human interleukin-2 DNA sequence or a modification of the human interleukin-2 DNA sequence that encodes a protein having: (a) an amino acid sequence that is at least substantially identical to the amino acid sequence of native human interleukin-2 including the disulfide bond of the cystines at positions 58 and 105, and (b) has biological activity that is common to native human interleukin-2. Substantial identity of amino acid sequences means the sequences are identical or differ by one or more amino acid alterations (deletions, additions, substitutions) that do not cause an adverse functional dissimilarity between the synthetic protein and native human interleukin-2. Examples of such proteins are the recombinant IL-2s described in European patent application No. 83101035.0 filed Feb. 3, 1983 (published Oct. 19, 1983 under publication No. 91539) and European patent application No. 82307036.2 filed Dec. 22, 1982 (published Sept. 14, 1983 under No. 88195), the recombinant IL-2 muteins described in European patent application No. 83306221.9 filed Oct. 13, 1983 (published May 30, 1984 under No. 109748) which is the equivalent to Belgian Pat. No. 893,016, commonly owned U.S. Pat. No. 4,518,584, and the recombinant IL-2s described in this application.

As used herein the term "transformed microorganism" denotes a microorganism that has been genetically engineered to produce a protein that possesses native human interleukin-2 activity. Examples of transformed microorganisms are described in said European patent publications Nos. 88,198; 91,539, 109,748 and U.S. Ser. No. 564,224. Bacteria are preferred microorganisms for producing IL-2. A typical transformed microorganism useful in the present invention is E. coli K-12 strain MM294 transformed with plasmid pLW1 (deposited at the American Type Culture Collection on Aug. 4, 1983 by Cetus Corporation under the provisions of the Budapest Treaty and having accession No. 39,405). Synthetic recombinant IL-2 may also be made by suitably transformed yeast and mammalian cells. *E. coli* is particularly preferred host organism.

FIG. 1 illustrates a flow diagram for processing and purifying microbially-produced recombinant IL-2. The description that follows provides further details of this flow diagram. Reference is also made to U.S. Ser. Nos. 594,351; 661,902; 594,223 and 594,250; the disclosures of which are incorporated herein by reference.

The transformed microorganisms are grown in a suitable growth medium, typically to an optical density (OD) of at least about 30 to 680 nm, and preferably between about 20 and 40 at 680 nm. The composition of the growth medium will depend upon the particular microorganism involved. The medium is an aqueous medium containing compound that fulfill the nutritional requirements of the microorganism. Growth media will typically contain assimilable sources of carbon and nitrogen, energy sources, magnesium, potassium and sodium ions, and optionally amino acids and purine and pyrimidine bases. (See *Review of Medical Biology*, Lange Medical Publications, 14th Ed pp 80-95 (1980.)) In expression vectors involving the trp promoter, the tryptophane concentration in the medium is carefully controlled to become limiting at the time IL-2 expression is desired. Growth media for *E. coli* are well known in the art. A preferred growth method is described in U.S. Pat. No. 4,499,188, granted Feb. 12, 1985.

After the cells are harvested from the culture, they may be concentrated, if necessary, to about 20 to 150 mg/ml, preferably 80 to 100 mg/ml (OD 40 to 300, preferably 160 to 200 at 680 nm) by filtration, centrifugation, or other conventional methods.

Following concentration the cell membranes of the microorganisms are disrupted. The main purpose of disruption is to facilitate the following extraction and solubilization steps. Conventional cell disruption techniques such as homogenization, sonication, or pressure cycling may be used in this step of the process. Preferred methods are sonication or homogenization with a Manton-Gaulin homogenizer. The end point of the disruption step may be monitored by optical density, with the optical density of the suspension typically decreasing about 65% to 85%. In any event, the disruption should break substantially all of the cells so that substantially no intact cells are carried through to the solubilization step. Before the disruption, the pH of the liquid phase of the concentrate is adjusted, if necessary, to a level that facilitates removal of *E. coli* proteins in subsequent steps, while retaining recombinant IL-2 protein as an insoluble complex in the cellular debris. The pH may be so adjusted by adding suitable buffers. In most instances pHs in the range of about 8 to about 8.5 will be used.

The steps in the recovery process subsequent to the disruption step as shown in FIG. 1 are primarily designed to separate the IL-2 from *E. coli* proteins to a high level of purity (preferably at least about 95% and more preferably at least about 98%) in good yields while maintaining the IL-2 in a reduced state. Simultaneously, these purification processes, in combination, also reduce pyrogenic substances in the final product to a level believed to be acceptable for parenteral administration to patients.

After the cells have been disrupted the particulate matter may be separated from the liquid phase of the disruptate and resuspended in an aqueous medium buffered to the optimal pH for the extraction. The particulate matter may optionally be washed with buffer at this stage to remove any water soluble *E. coli* proteins therein. In any event, the protein concentration of the cell suspension subjected to the extraction will usually be in the range of about 5 to about 60 mg/ml, preferably 20 to 40 mg/ml.

The extraction of *E. coli* proteins from the particulate cellular material may be carried out concurrently with the disruption or sequentially following the disruption. It is preferably carried out as a step following the disruption. The extractant is an aqueous solution of a chaotropic agent (i.e., a mild protein denaturant that dissociates hydrogen bonds and affects the tertiary structure of proteins). The extractant selectively removes the bulk of the *E. coli* proteins from the cellular debris leaving at least a substantial portion of the recombinant IL-2 associated (contained in or bound to) with the cellular debris. The selectivity is facilitated by the hydrophobicity of the recombinant IL-2 and the fact that it is in a reduced, insoluble state at a pH near the isoelectric point of the protein. In addition, a substantial portion of the recombinant IL-2 may be present in in vivo as inclusion bodies of significant mass, as has been the case with other cloned proteins expressed at high levels in *E. coli*. Examples of extractants are urea and guanidinium hydrochloride (guanidinium hydrochloride should not be used when SDS is used as a solubilizing agent). Urea is preferred. The concentration of the chaotropic agent in the extraction mixture will depend upon the particular agent that is used and the amount of cellular material in the extraction mixture. In the case of urea, concentrations (final) between about 3.5 M and 4.5 M, preferably about 4 M, will be used in batch processes at 25° C. If the extraction is run on a continuous basis over longer time periods it may be desirable to use lower concentrations. Temperatures in the range of 20° C. to 25° C. will normally be used in extraction, with room temperature being used for convenience. Mixing will typically be used to enhance contact between the solution and particulate matter and thus decrease the time required to extract non-IL-2 proteins from the cellular debris. Kinetic analysis of the extraction process was performed on the supernatants using SDS-PAGE, and the extraction was found to be essentially complete by 15-30 minutes.

Following the extraction, the mixture is separated into solid and liquid phases. The recombinant IL-2 in the solid phase is then selectively solubilized by contacting the solid phase with a neutral, aqueous buffer containing a reducing agent and a solubilizing agent. Physiologically acceptable surface active agents (detergents) that have a suitable hydrophobic-hydrophilic balance to solubilize the hydrophobic recombinant IL-2 may be used. Alkali metal sulfates containing 10 to 14 carbon atoms and alkali metal alkyl sarcosinates are preferred solubilizing agents, with SDS and sarcosyl being particularly preferred.

The amount of solubilizing agent used in the solubilization will depend upon the particular agent. When SDS or sarcosyl are used, the preferred ratio (w/w) of SDS/sarcosyl to solid phase protein is about 0.5:1 to 1.4:1. The solubilizing medium also contains a sufficient amount of reducing agent to prevent the solubilized IL-2 from undergoing oxidation to any significant degree. Protein reducing agents such as dithiothreitol (DTT) and 2-mercaptoethanol may be used. The concentration of reducing agent such as DTT in the medium will usually range between about 5 to 20 mM. The solubilization will typically be carried out at temperatures in the range of 20° C. to 25° C. with mixing to facilitate contact between the solid phase and the solubilizing medium. Higher temperatures may solubilize unwanted E. coli proteins. The solubilization is considered complete when the sample has sat 15 minutes or the solution turns translucent. Insoluble material is separated after completing the solubilization.

After the IL-2 is solubilized the IL-2 may optionally be extracted from the aqueous solution under reducing conditions with 2-butanol or 2-methyl-2-butanol to remove additional E. coli proteins, notably including certain contaminants that have molecular weights very close to the IL-2. Conditions (e.g., ionic strengths in the range of 0.05 and 0.15) at which the aqueous solution and butanol are substantially immiscible are used. In carrying out the organic extraction the protein concentration of the aqueous solution is preferably adjusted, if necessary, to less than about 6 mg/ml, preferably about 0.5 to 4 mg/ml. Reducing conditions are maintained by carrying out the extraction in the presence of a reducing agent (e.g., DTT). The butanol will normally be added to the aqueous solution of solubilized IL-2 in volume ratios in the range of about 1:1 to about 3:1 (extractant-:aqueous solution), preferably about 1:1. The extraction may be carried out in a batch or continuous operation. The temperature will normally be in the range of 20° C. to 100° C. and the pH will normally be about 4 to 9, preferably about 5 to 6. The time of contact between the solution and the butanol is not critical and relatively short times on the order of a few minutes may be used. After the extraction is complete, the aqueous phase and butanol phase are separated and the IL-2 is separated from the butanol phase. A preferred procedure for separating the IL-2 from the butanol phase is acid precipitation. This is done by adding the butanol phase to aqueous buffer, pH 7.5 until the organic phase is dissolved (approx. 2-3 vol buffer per vol of organic), and then lowering the pH to about 5.5 to 7.0, preferably 6.0 to 6.2, to cause the IL-2 to precipitate.

The next step in the process is to separate the recombinant IL-2 and any E. coli contaminants remaining after the extraction(s) and optimally from the solubilizing agent. Gel filtration chromatography, RP-HPLC, or a combination of gel filtration chromatography and RP-HPLC are used. The gel filtration chromotographic is preferably carried out in two stages that remove pyrogenic components and protein contaminants having molecular weights higher or lower than recombinant IL-2. (Recombinant IL-2 has a molecular weight of about 15.5K daltons.) Gels that are capable of fractionating the solution to permit separation of the IL-2 from these contaminants are commercially available. Sephacryl S-200 is a preferred gel for removing the higher molecular weight components and Sephadex G-25, G-75 or G-100 gels are preferred for moving the low molecular weight contaminants. The gel filtrations will typically be run in buffered solutions (pH 5.5 to 7.0) containing about 0.1% to 1.0% solubilizing agent and about 1 to 10 nM reducing agent. The column will be sized to permit suitable resolution of the desired components.

RP-HPLC is an alternative to gel filtration. Also, RP-HPLC is capable of removing molecules from the solution that have molecular weights close to recombinant IL-2 and cannot, therefore, be removed completely by gel filtration. In addition, contaminants such as bacterial endotoxin are also removed effectively by RP-HPLC. Therefore, RP-HPLC may also be used as a final purification step after gel filtration. Supports (stationary phases) that provide good resolution of proteins may also be used as a final purification step after gel filtration. Supports (stationary phases) that provide good resolution of proteins may be used in the RP-HPLC. C-4, C-8, or C-18 on 300 angstrom pore-size supports are examples of preferred supports. The separation is carried out at an acidic pH of less than about 2.3, usually 2.1 to 2.3 in order to keep the IL-2 in solution. In this regard, the pH of the solution from the solubilization (gel filtration) will preferably be adjusted to this range. The solution is loaded into the RP-HPLC column and is absorbed onto the stationary phase. A gradient solvent system comprising an organic acid such as acetic acid or trifluoroacetic acid and organic solvent such as propanol or acetonitrile is used to elute the recombinant IL-2 from the column. Acetic acid-propanol, trifluoroacetic acid-propanol, and trifluoroacetic acid-acetonitrile are preferred solvent systems. Recombinant IL-2 elutes in the acetic acid-propanol system at about 40% propanol, in the trifluoroacetic acid-propanol system at about 50% propanol, and in the trifluoroacetic acid-acetonitrile system at about 62% acetonitrile. For convenience, the organic solvent content of the elutant will usually be increased rapidly to a level somewhat below the solvent concentration at which the recombinant IL-2 elutes followed by a slow gradient change in the range of about 0.1% to 1.0%/min.

As soon as the recombinant IL-2 is recovered from the chromatography step, it is lyophilized and resuspended in a neutral aqueous buffer containing the reducing agent (to keep the recombinant IL-2 in a reduced state) and the solubilizing agent (to keep it in solution). The recombinant IL-2 is stable in this form and may be stored for further treatment and formulation before being used.

An alternative and preferred procedure is to selectively oxidize, under controlled conditions, the recombinant IL-2 after it has been separated by gel filtration and purify the oxidized product by RP-HPLC or gel filtration followed by RP-HPLC. This results in efficient removal of contaminants surviving the gel filtration as well as unwanted oxidation products. A preferred oxidation procedure is to selectively oxidize a fully reduced microbially produced synthetic recombinant IL-2 protein having an amino acid sequence substantially identical to the recombinant IL-2 protein which sequence includes cysteines which in the useful protein are linked intramolecularly at positions 58 to 105 to form a cystine in a controlled manner so that the cysteines are oxidized selectively to form the cystine at positions 58 and 105. The efficiency of the controlled and selective oxidation is improved if a recombinant IL-2 mutein is used such as described and claimed in Belgian Pat. No. 898,016 and U.S. Pat. No. 4,518,584. In such case the cysteine at position 125 is deleted or replaced with a neutral amino acid thus preventing incorrect intramolecular bonds and/or intermolecular bonds with the cysteine at position 125 during oxidation which may also form dimers or polymers of IL-2. In this process the fully reduced microbially produced synthetic recombinant IL-2 protein is preferably reacted with o-iodosobenzoate, which oxidizes cysteines selectively in an aqueous medium, at a pH at least about one-half pH unit below the $pK_a$ of said cysteines, wherein the concentration of synthetic protein in the reaction mixture is less than about 5 mg/ml and the mol ratio of o-iodosobenzoate to protein is at least stoichiometric, with the proviso that the o-iodosobenzoate is in excess in the terminal portion of the reaction. This selective oxidation produces a biologically active molecule. RP-HPLC purification of the selectively oxidized product may be carried out under the conditions described above in the absence of a reducing agent and presence of a detergent at a concentration equal to or less than those used in the above described gel filtration.

The purity of the recombinant IL-2 after the chromatography step(s) is at least about 95% and usually at least about 98%. This highly pure material contains less than about 5 ng endotoxin, usually less than about 0.01 ng endotoxin per 100,000 Units IL-2 activity.

The formulation of recombinant IL-2 in accordance with this invention may be carried out as a separate operation using purified, selectively oxidized IL-2 or in an operation that is integrated with the purification of the selectively oxidized IL-2. In the latter case, the starting material for the formulation is a recombinant IL-2-containing product from a reverse phase high performance liquid chromatography (RP-HPLC) treatment of the selectively oxidized product, preferably recombinant IL-2 selectively oxidized by the RP-HPLC product (pool) will comprise a solution of recombinant IL-2 in a water-organic solvent mixture. The nature of the organic solvent will depend upon the solvent system used in RP-HPLC. Examples of systems that may be used are combinations of an organic acid such as acetic acid or trifluoroacetic acid and organic solvent such as propanol or acetonitrile.

The first step in formulating the recombinant IL-2 from such an RP-HPLC pool is to render the mixture aqueous by resuspending (diluting) the pool in an aqueous buffer containing a detergent, such as SDS or sarcosyl, that enhances the solubility of the recombinant IL-2 in water. Following this dilution the organic phase is removed from the recombinant IL-2 containing aqeuous phase and the detergent concentration is reduced by diafiltration using an appropriate buffer. When SDS is used, the SDS is reduced to a level of about 100 to 250, preferably approximately 200, µg/mg IL-2. Following diafiltration, the IL-2 concentration is readjusted to a concentration in the range of about 0.01 to 2 mg/ml and the water soluble carrier is added to the desired level. The carrier will typically be added such that it is present in the solution of about 1 to 10% by weight, preferably about 5% by weight. The exact amount of carrier added is not critical. Conventional solid bulking agents that are used in pharmaceutical tablet formulation may be used as the carrier. These materials are water soluble, do not react with the IL-2, and are themselves stable. They are also preferably non-sensitive (i.e., nonhygroscopic) to water. Examples of carriers that may be added are lactose, mannitol, and other reduced sugars such as sorbitol, starches and starch hydrolysates derived from wheat, corn, rice, and potato, microcrystalline celluloses, and albumin such as human serum albumin. Mannitol is preferred.

The carrier adds bulk to the formulation such that when unit dosage amounts of the solution are lyophilized in containers, such as sterile vials, the freeze-dried residue will be clearly discernible to the naked eye. In this regard the preferred carrier, mannitol, yields an aesthetically acceptable (white, crystalline) residue that is not sensitive to water. The nonsensitivity of mannitol to water may enhance the stability of the formulation.

After adding the carrier the unit dosage amounts (i.e., volumes that will provide 0.01 to 2 mg, preferably 0.2 to 0.3 mg, IL-2 per dose) of the solution are dispensed into containers, the containers are capped with a slotted stopper, and the contents are lyophilized using conventional freeze-drying conditions and apparatus.

The lyophilized, sterile product consists of a mixture of (1) recombinant IL-2, (2) carrier (mannitol), (3) detergent (SDS), and (4) a small amount of buffer that will provide a physiological pH when the mixture is reconstituted. The recombinant IL-2 will typically constitute about 0.015% to 3.85% by weight of the mixture, more preferably about 0.4% to 0.6% of the mixture. Storage tests of this product indicate that the IL-2 is stable in this form for more than three months at 2° C. to 8° C.

The lyophilized mixture may be reconstituted by injecting a conventional parenteral aqueous injection such as water for injection, Ringer's injection, dextrose injection, dextrose and salt injection, or the like, into the vial. The injection should be added against the side of the vial to avoid excess foaming. The amount of injection added to the vial will typically be in the range of 1 to 5 ml, preferably 1 to 2 ml.

The reconstituted formulation is suitable for parenteral administration to humans or other mammals to provide IL-2 therapy thereto. Such therapy is appropriate for a variety of immunomodulatory indications such as T cell mutagenesis, induction of cytotoxic T cells, augmentation of natural killer cell activity, induction of IFN-gamma, restoration or enhancement of cellular immunity (e.g., treatment of immune deficient conditions), and augmentation of cell mediated anti-tumor activity.

The following example further illustrates the invention. This example is not intended to limit the invention in any manner.

EXAMPLE

The recombinant IL-2 used in this example is des-ala IL-2$_{ser125}$. The amino acid sequence of this IL-2 differs from the amino acid sequence of native human IL-2 in that it lacks the initial alanine of the native molecule and the cysteine at position 125 has been changed to serine. Samples of *E. coli* that produce this IL-2 have been deposited by Cetus Corporation in the American Type Culture Collection, 12301 Parklawn Drive, Rockville, Md., USA, on Sept. 26, 1983 under accession No. 39452 and on Mar. 6, 1984 under accession number 39626 under the provisions of the Budapest Treaty.

329 mg of an RP-HPLC purified cysteine oxidized IL-2 product (protein concentration 0.94 mg/ml) in 60% 2-propanol, 6% acetic acid was diluted ten-fold into 50 mM sodium acetate, 1 mM ethylene diamine tetraacetic acid (EDTA), 0.1% sodium dodecyl sulfate (SDS) at pH 5.5.

The recombinant IL-2 solution was then concentrated using a 10 sq. ft. hollow fiber cartridge (nominal molecular weight cut-off 10,000 daltons) to a volume of 600 ml and then diafiltered for 3 volumes against 50 mM sodium acetate, 1 mM EDTA, 0.1% SDS at 5.5. The material was then further diafiltered against 10 mM sodium phosphate containing 5 µg SDS/ml until the residual SDS reached a value of 131 µg SDS/mg protein. Approximately 255 mg IL-2 at a concentration of 0.6 mg/ml were recovered (425 ml).

Only 222 mg were used for the formulation which was carried out as follows: 370 ml of the IL-2 solution (222 mg, 0.6 mg/ml) was diluted with 10 mM sodium phosphate, pH 7.5 and 20% mannitol such that the final composition was:

| 0.25 mg/ml IL-2 | in 10 mM sodium phosphate, pH 7.5 |
| 5% mannitol | |

The solution was then sterile filtered through a 0.2 micron filter, filled into sterile vials (1.2 ml fill volume) and lyophilized. The product was sealed under vacuum.

The thus produced formulation has been used clinically in humans and has been well tolerated at dosages up to 2 million units/m² when administered as a continuous intravenous infusion or up to 1 million units/m² when administered as an intravenous or intramuscular bolus. Suitable indications for use of the recombinant IL-2 include:

(1) treatment of immunodeficiency states, acquired, inborn, or induced by chemotherapy, immunotherapy, or irradiation;

(2) enhancement of cell-mediated immune responses in the therapy of viral, parasitic, bacterial, malignant, fungal, protozoal, or mycobacterial or other infectious diseases;

(3) induction of enhanced immunologic response of cells ex vivo in the treatment of infectious, malignant, rheumatic, or autoimmune diseases;

(4) treatment of rheumatoid or other inflammatory arthridites;

(5) treatment of diseases of abnormal immune response such as multiple sclerosis, systemic lupus erythematosis, glomerulonephritis, or hepatitis;

(6) regulation of hematopoietic tumors or pre-malignant or aplastic abnormalities of hematopoietic tissue;

(7) use as an adjuvant in induction of cell-mediated or humoral response to naturally occurring, administered natural, chemically synthesized or modified, or recombinantly engineered vaccines or other antigens administered for therapeutic purposes;

(8) use as a mediator of neurotransmission or as a psychoactive therapeutic, as an enkephalin for therapeutic purpose, or as a modifier of central nervous system function;

(9) in a topical application for the treatment of above-mentioned disease states;

(10) in combination with cytotoxic chemotherapy or irradiation or surgery in the treatment of malignant or pre-malignant diseases in a direct therapeutic or adjuvant setting;

(11) in combination with agents with direct anti-viral, anti-fungal, anti-bacterial, or anti-protozoal activity or in combination with drug therapy for typical and atypical m. tuberculosis;

(12) in combination with other immune-modulating drugs, lymphokines, (e.g., Il-1,Il-3, CSF-1, alpha-interferons, and gamma-interferons) naturally occurring or inducible anti-cellular toxins or molecules which mediate lysis or stasis or malignant cells in the treatment of malignant, infectious, autoimmune, or rheumatic diseases; and

(13) for prophylaxis against infectious diseases.

In a similar manner, recombinant IL-2 proteins of the wild-type as disclosed in European patent publication No. 91,539 or the oxidation resistant muteins wherein methionine(s) has been replaced by another amino acid disclosed in U.S. Ser. No. 692,596, filed Jan. 18, 1985, the disclosure of which is incorporated herein by reference, may be formulated in accordance with the present invention. All forms of IL-2, whether of the wild-type or native form or muteins thereof, are contemplated to be within the scope of the present invention.

Modifications of the above-described modes for carrying out the invention that are obvious to those of skill in the field of pharmaceutical formulation or related fields are intended to be within the scope of the following claims.

What is claimed is:

1. A recombinant IL-2 composition suitable for reconstituting in a pharmaceutically acceptable aqueous vehicle for parenteral administration to a patient to provide IL-2 therapy comprising a sterile lyophilized mixture of:

(a) a therapeutically effective amount of a selectively oxidized microbially produced recombinant IL-2 that is substantially free of non-IL-2 protein, and it is at least 95% pure recombinant IL-2, and contains less than about 5 ng endotoxin per 100,000 units of IL-2 activity;

(b) a physiologically acceptable water soluble carrier that does not affect the stability of the selectively oxidized microbially produced IL-2 adversely; and (c) a sufficient amount of a surface active agent to ensure the water solubility of the selectively oxidized, microbially produced hydrophobic recombinant IL-2.

2. The composition of claim 1 wherein the oxidized microbially produced recombinant IL-2 includes less than about 5% by weight non-IL-2 protein and the surface active agent is sodium dodecyl sulfate (SDS) or sodium deoxycholate.

3. The composition of claim 1 wherein the oxidized microbially produced IL-2 constitutes about 0.02% to 3.85% by weight of the mixture.

4. The composition of claim 1 wherein the recombinant IL-2 is des ala IL-2$_{ser125}$.

5. The composition of claim 1 wherein the water soluble carrier is mannitol.

6. The composition of claim 2 wherein the sodium dodecyl sulfate is present at about 100 to about 250 μg per mg of IL-2.

7. The composition of claim 2 wherein the recombinant IL-2 is des ala IL-2$_{ser125}$, the recombinant IL-2 protein includes less than about 5% by weight non-IL-2 protein, the IL-2 constitutes about 0.015% to 3.85% by weight of the mixture, the water soluble carrier is mannitol, and the sodium dodecyl sulfate is present at about 100 to about 250 μg per mg of IL-2.

8. A pharmaceutical composition for providing therapy to a patient comprising a sterile solution of:

(a) the mixture of claim 1 dissolved in (b) a pharmaceutically acceptable aqueous parenteral injection, said solution containing in the range of about 0.01 mg to about 2 mg of the selectively oxidized microbially produced recombinant IL-2 ml.

9. A pharmaceutical composition for providing IL-2 therapy to a patient comprising a sterile solution of:

(a) the mixture of claim 2 dissolved in (b) a pharmaceutically acceptable aqueous parenteral injection, said solution containing in the range of about 0.01 mg to about 2 mg of the selectively oxidized microbially produced recombinant IL-2 ml.

10. A pharmaceutical composition for providing IL-2 therapy to a patient comprising a sterile solution of:

(a) the mixture of claim 3 dissolved in
(b) a pharmaceutically acceptable aqueous parenteral injection, said solution containing in the range of about 0.01 mg to about 2 mg of the selectively oxidized microbially produced recombinant IL-2 per ml.

11. A pharmaceutical composition for providing IL-2 therapy to a patient comprising a sterile solution of:
(a) a mixture of claim 4 dissolved in
(b) a pharmaceutically acceptable aqueous parenteral injection, said solution containing in the range of about 0.01 mg to about 2 mg of the selectively oxidized microbially produced recombinant IL-2 per ml.

12. A pharmaceutical composition for providing IL-2 therapy to a patient comprising a sterile solution of:
(a) the mixture of claim 5 dissolved in
(b) a pharmaceutically acceptable aqueous parenteral injection, said solution containing in the range of about 0.01 to about 2 mg of the selectively oxidized microbially produced recombinant IL-2 per ml.

13. A pharmaceutical composition for providing IL-2 therapy to a patient comprising a sterile solution of:
(a) the mixture of claim 6 dissolved in
(b) a pharmaceutically acceptable aqueous parenteral injection, said solution containing in the range of about 0.01 mg to about 2 mg of the selectively oxidized microbially produced recombinant IL-2 per ml.

14. A pharmaceutical composition for providing therapy to a patient comprising a sterile solution of:
(a) the mixture of claim 7 dissolved in
(b) a pharmaceutically acceptable aqueous parenteral injection, said solution containing in the range of about 0.01 mg to about 2 mg of the selectively oxidized microbially produced recombinant IL-2 per ml.

15. The pharmaceutical composition of claim 8 wherein the aqueous parenteral vehicle is water for injection.

* * * * *